(12) United States Patent
Molina (10) Patent No.: US 11,020,266 B1
(45) Date of Patent: Jun. 1, 2021

(54) ANTI-SNORING SYSTEM

(71) Applicant: Jose B Molina, Miami, FL (US)

(72) Inventor: Jose B Molina, Miami, FL (US)

( * ) Notice: Subject to any disclaimer, the term of this patent is extended or adjusted under 35 U.S.C. 154(b) by 0 days.

(21) Appl. No.: 17/142,086

(22) Filed: Jan. 5, 2021

(51) Int. Cl.
| | | |
|---|---|---|
| *A61F 5/56* | (2006.01) | |
| *A47C 21/00* | (2006.01) | |
| *A61G 7/065* | (2006.01) | |
| *A61G 7/07* | (2006.01) | |
| *A61H 1/00* | (2006.01) | |
| *A61H 23/00* | (2006.01) | |

(52) U.S. Cl.
CPC .............. *A61F 5/56* (2013.01); *A47C 21/006* (2013.01); *A61G 7/065* (2013.01); *A61G 7/07* (2013.01); *A61H 1/005* (2013.01); *A61H 23/00* (2013.01)

(58) Field of Classification Search
CPC ......... A61F 5/56; A47C 21/006; A61G 7/065; A61G 7/07; A61H 1/005; A61H 23/00; A61H 2201/0134; A61H 23/004
USPC ................ 128/848, 871; 601/30, 46, 56, 57
See application file for complete search history.

(56) References Cited

U.S. PATENT DOCUMENTS

| | | | | |
|---|---|---|---|---|
| 2,943,620 A * | 7/1960 | Sibert | ................... | A61H 23/02 601/18 |
| 4,136,685 A * | 1/1979 | Ramey | ............................. | 5/915 |
| 4,559,929 A * | 12/1985 | Hseu | ................... | A61H 23/0263 366/111 |
| 4,941,478 A * | 7/1990 | Takeuchi | .................. | A61F 5/56 128/848 |
| 5,081,447 A * | 1/1992 | Echols | ...................... | A61F 5/56 200/DIG. 2 |
| 5,381,801 A * | 1/1995 | McShane | .................. | A61F 5/56 128/848 |
| 5,429,585 A * | 7/1995 | Liang | .................. | A61H 23/0263 600/9 |
| 5,797,860 A * | 8/1998 | Moriyasu | ............... | A61H 1/005 5/420 |
| 6,057,767 A * | 5/2000 | Barnoach | .................. | A61F 5/56 340/573.1 |
| 6,968,806 B2 * | 11/2005 | Helwig | ................ | A01K 1/0353 119/28.5 |
| 8,783,264 B2 * | 7/2014 | Levendowski | ...... | A61B 5/4806 128/871 |
| 9,357,855 B2 * | 6/2016 | Gersin | ............... | A61H 23/0263 |
| 9,968,238 B2 * | 5/2018 | Patel | ..................... | A47L 23/266 |
| 10,610,142 B1 * | 4/2020 | Diju | ...................... | A61M 5/422 |
| 10,653,366 B2 * | 5/2020 | Levine | ...................... | A61F 9/04 |
| 2002/0095104 A1 * | 7/2002 | Chen | ..................... | A61H 23/02 601/56 |

* cited by examiner

*Primary Examiner* — Keri J Nelson
(74) *Attorney, Agent, or Firm* — Ruben Alcoba, Esq.

(57) ABSTRACT

An anti-snoring system that promotes an individual's prolonged sleep. The anti-snoring system is comprised of a vibrating device that is placed on an anti-slip mat that is in turn placed on a position of a bed that will prevent a side sleeper from resting on his or her back. The anti-snoring system promotes side sleeping, a position that maximizes an individual's air intake while sleeping.

5 Claims, 8 Drawing Sheets

ANTI-SNORING SYSTEM

RELATED APPLICATIONS

This application claim priority of U.S. Provisional Patent Application No. 63/061,371 that was filed on Aug. 5, 2020 by Jose B Molina, the subject matter, the description, and the drawings of the provisional application are incorporated herein by reference.

BACKGROUND

The present invention is directed to a device that will minimize the snoring of an individual while sleeping on a bed.

The inventor of the present invention has suffered from a sleep disorder for over the past 35 years. The sleep disorder would cause him to fall asleep during daylight hours and in unusual places.

As he got older, his sleep disorder became worse and he sought medical help to help him treat the disorder. They diagnosed that he has a large/long uvula and recommended surgery to treat the disorder. The inventor complied with the treatment, yet it was to no avail. His sleep patterns were still disrupted because of his snoring and possible lack of oxygen.

After the procedure he tried other devices to alleviate his snoring, for example jaw straps. His experience with the straps was not pleasant, for he choked when wearing the straps. He also tried specialized pillows and beds to prevent snoring, they were also not the solution.

One day he realized that when he slept on his side, he was able to sleep for longer periods of time and his snoring patterns were considerably reduced. He also realized that the moment that he would roll on his back he would commence snoring, his wife informed him, and that shortly thereafter he would stop breathing intermittently and would awaken.

The above revelation led him to research the subject and he discovered the facts about snoring and sleep apnea. The Mayo Clinic made a report that specifically stated that when an individual sleeps on his or her back, that the individual's normal airway collapse is further aggravated.

The information he gathered led him to realize that if he wanted to sleep for a prolonged period, that he would have to sleep on his side and to avoid sleeping on his back.

He tried many things to force himself to remain on his side, for example, placing a bottle around a belt that he would wear to sleep to see if the crumpling sound of the belt would awaken him when laying on his back, the bottle-belt conception did not work. He then believed that by placing uncomfortable objects on the back of a garment that he slept in would prevent him from rolling to his back that the objects would force him to roll back to the side position, this also failed. He next conceived of a mat that would deliver an electric charge when he rolled into the back position, it was effective in, getting him off the mat, yet it would awaken him and defeated the purpose of getting a long night's sleep.

Through trial and error, the inventor conceived the present invention which is a vibrating and buzzing device that one lays on a position of a bed that would gently force a person laying on the device to roll back into the position that they were in prior to laying on the device. The gentle vibrating and buzzing device would minimize the chances of the person laying on the device from awakening.

The device of the present invention addresses the need of having a device that will assist a person who sleeps on his or her side to remain on the side in which they were sleeping in, thereby minimizing the frequency of the snoring and it also lessened the loudness of the snoring.

SUMMARY

The present invention is an anti-snoring system that promotes an individual's prolonged sleep. The anti-snoring system is comprised of a vibrating device that is placed on an anti-slip mat that is in turn placed on a position of a bed that will prevent a side sleeper from resting on his or her back. The anti-snoring system promotes side sleeping, a position that maximizes an individual's air intake while sleeping.

An object of the present invention is to promote side sleeping.

Another object of the present invention is to prolong the sleep cycle of a person who snores or suffers from sleep apnea.

Yet another object of the present invention is to prevent a person from sleeping on his back for any prolonged period.

Still another object of the present invention is to allow a person who suffers from sleep apnea to reduce the chances of coming down with illnesses that are associated with sleep apnea.

DRAWINGS

These and other features, aspects, and advantages of the present invention will become better understood with regards to the following description, appended claims, and drawings where:

DESCRIPTION

As seen in FIGS. 1-9, the present invention is an anti-snoring system that aids individuals sleep on their sides.

The anti-snoring system comprises of a rectangular plate 10, the rectangular plate 10 can be a plastic sheet of material. A raised rectangular frame 20 that defines a rectangular aperture 20a that is affixed to the rectangular plate 10. A rectangular printed circuit board 30 that defines a plurality of sensors 32 that are placed on a periphery of the printed circuit board 30. The printed circuit board 30 has a first pair of vibrating motors 34 and a second pair of vibrating motors 36, the vibrating motors 34, 36 are placed on the printed circuit board 30 so that the first pair of the vibrating motors 34 are linearly aligned on a first side 30a of the printed circuit board 30 and the second pair of the vibrating motors 36 are linearly aligned on a second side 30b of the printed circuit board 30. A battery receiver 38 that is positioned at a central location of the printed circuit board 30. The printed circuit board 30 operatively powers and connects the plurality sensors 32, the first pair of vibrating motors 34, and the second vibrating motors 36. A battery case 40 is affixed to the rectangular printed circuit board 30 around the battery receiver 38. A first pair of raised adhesive, rectangular strips 33 are attached to the first side 30a of the printed circuit board 30 and a second pair of raised adhesive rectangular strips 35 are attached to the second side 30b of the printed circuit board 30. A first pair of flat covers 42 are attached to the first pair of raised adhesive strips 33, the first pair of flat covers 42 cover at least two sensors 32 and each of the first pair of flat covers 42 define apertures 42a that allose the first pair of vibrating motors 34 to pass through them when the first flat covers 42 are pressed toward the printed circuit board 30. A second pair of flat covers 44 are attached to the second pair of raised adhesive strips 35, the second pair of flat covers 44 cover at least two sensors 32 and each of the second pair of flat covers 44 define apertures 44a that allow the second pair of vibrating motors 36 to pass through them when the second flat covers 44 are pressed toward the printed circuit board 30. At least one battery 50 that is placed in the battery receiver. A battery cover 52 that removably covers the battery case 40. A pouch 60 covers all of the elements described above after they have been assembled. And, a non-slip rectangular strip of fabric 70 that receives the pouch 60 after the non-slip rectangular strip 70 of fabric is placed on a bed 200 or sleeping surface.

In an embodiment of the present invention, the battery cover 52 is attached to the battery case 40 via hook and loop fasteners 41.

In another embodiment of the present invention the plurality of sensors 32 equals eight, and two sensors 32 are placed around each vibrating motor 32 or 34, and each flat cover 42 or 44 covers the two sensors 32, the flat covers 42 or 44 do not touch the sensors 32 unless a weight is applied to the flat covers 42 or 44. When the flat covers 42 or 44 are pressed onto the sensors 32, the vibrating motors 34 or 36 are triggered to vibrate, thereby making a buzzing noise.

Figure 1:
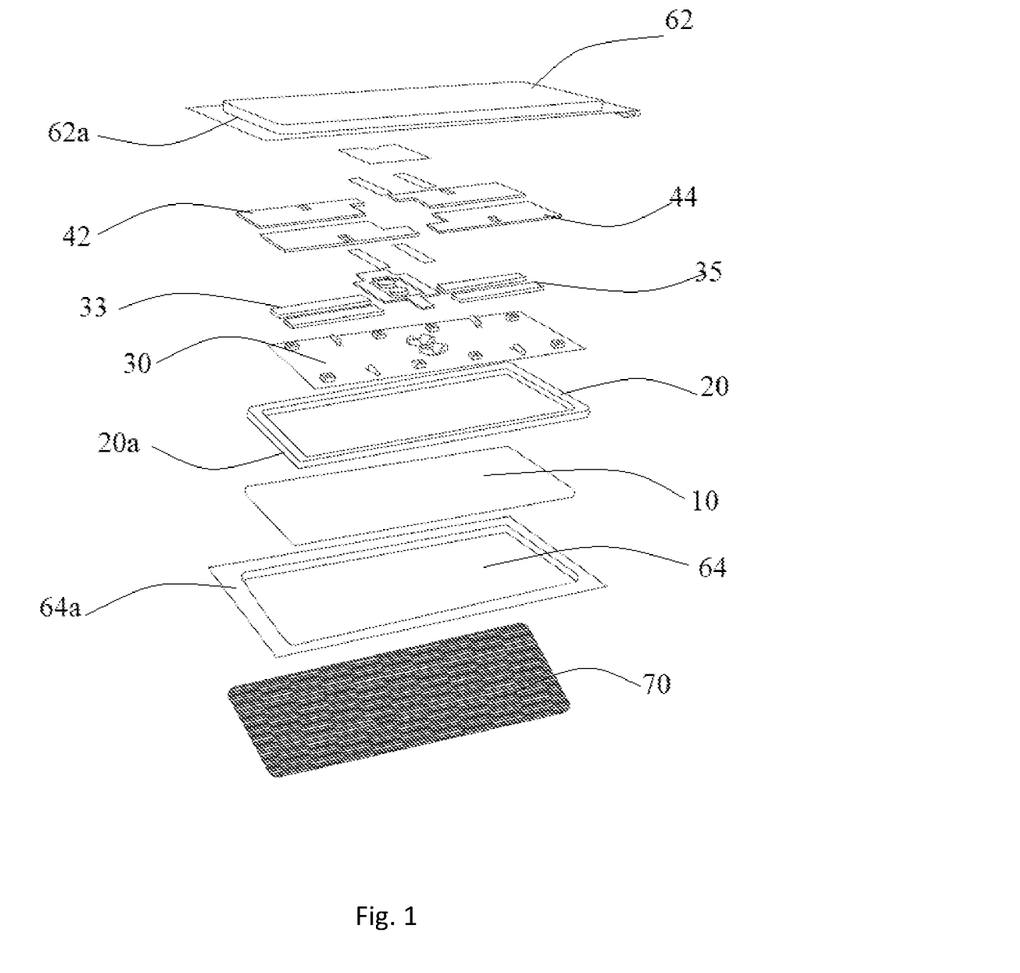
FIG. 1 shows an exploded view of an anti-snoring system.
Figure 2:
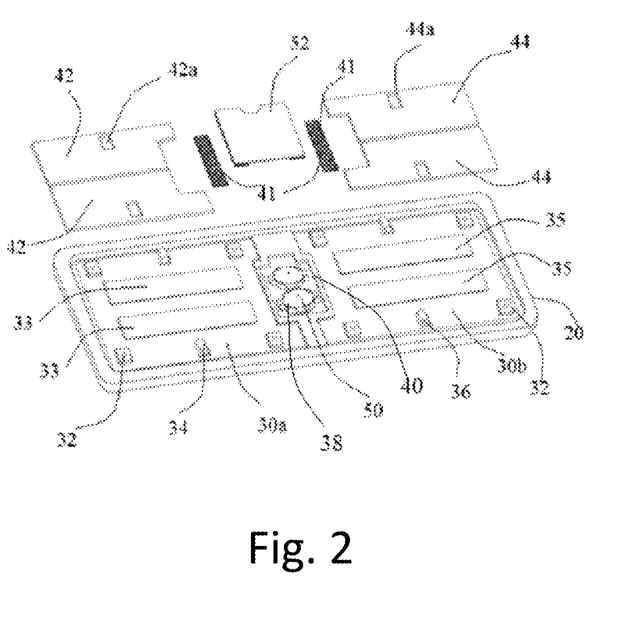
FIG. 2 shows a perspective view of the vibrating element, of the present invention that features some exploded elements.
Figure 3:
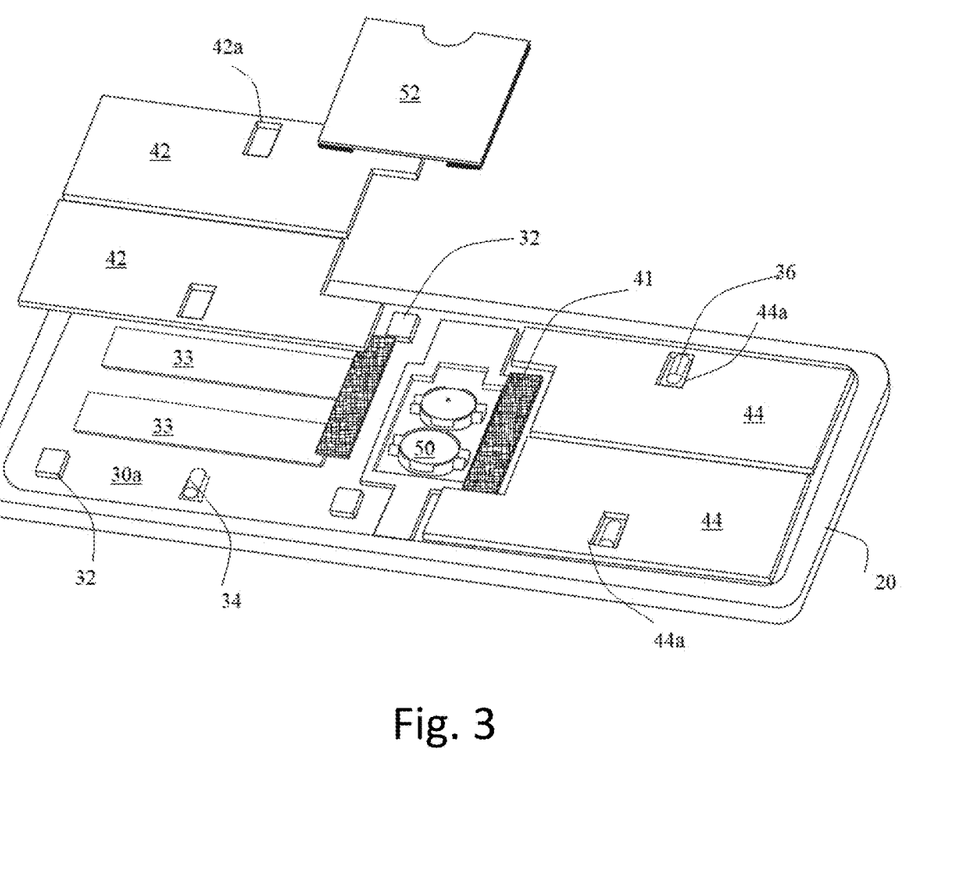
FIG. 3 shows a perspective view of the present invention that shows how the flat covers of the present invention are attached to the vibrating element of the present invention.
Figure 4:
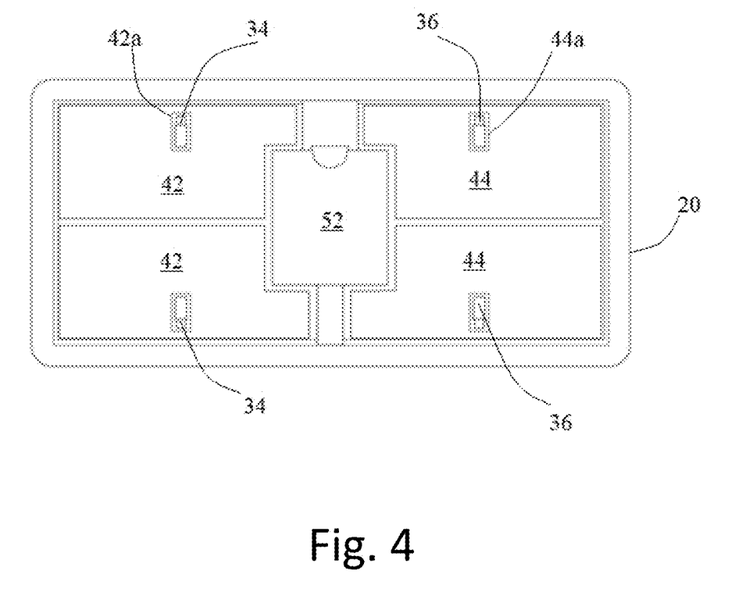
FIG. 4 shows a top plan view of the vibrating element of the present invention.
Figure 5:
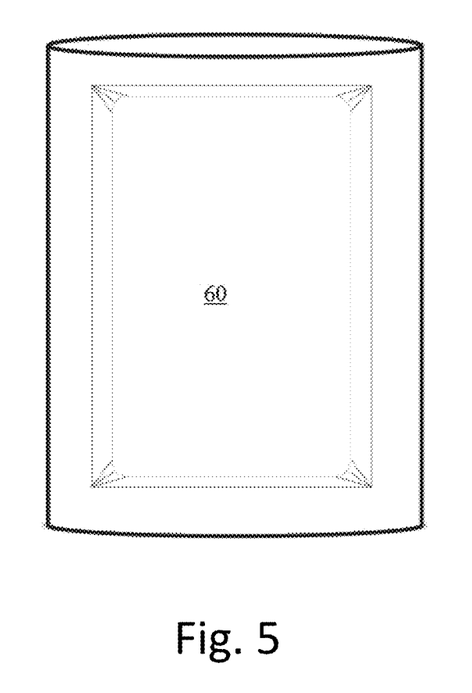
FIG. 5 shows a perspective view of the pouch or case of the present invention.

In a further embodiment of the present invention the pouch 60 is comprised of an upper fabric cover 62 that has hook and loop attachments 62a around a periphery of the first upper fabric cover 62 and a lower fabric cover 64 that has hook and loop attachments 64a around a periphery of the lower fabric cover 64, the upper fabric cover 62 and the lower fabric cover 64 are attached to each other.

Figure 6:
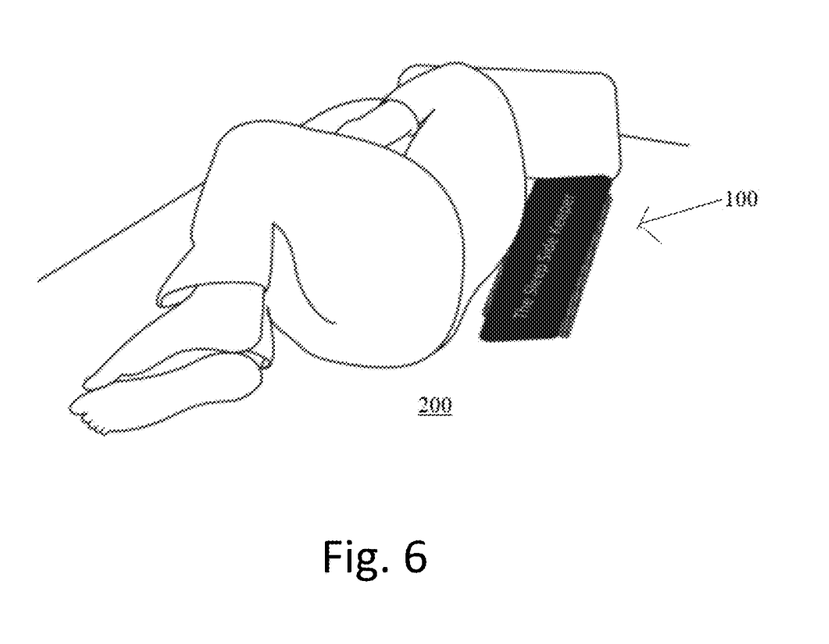
FIG. 6 shows a side sleeper on a bed and the present invention is to the right of the side sleeper.
Figure 7:
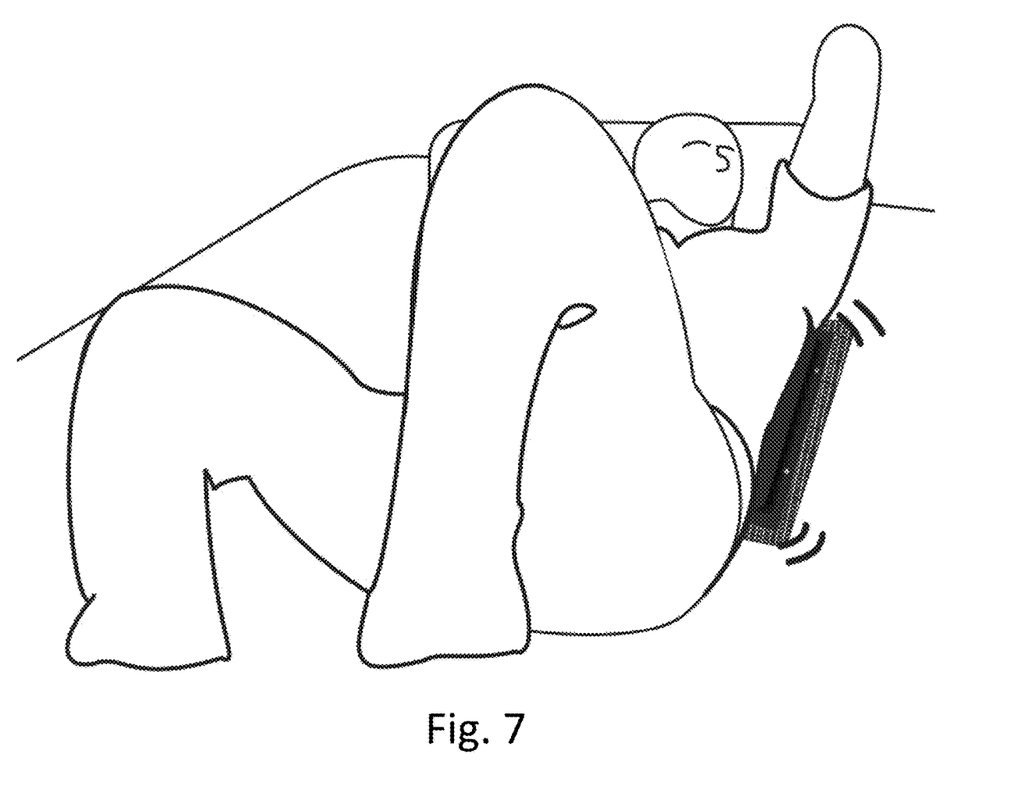
FIG. 7 shows the side sleeper on his back and on top of the present invention.
Figure 8:
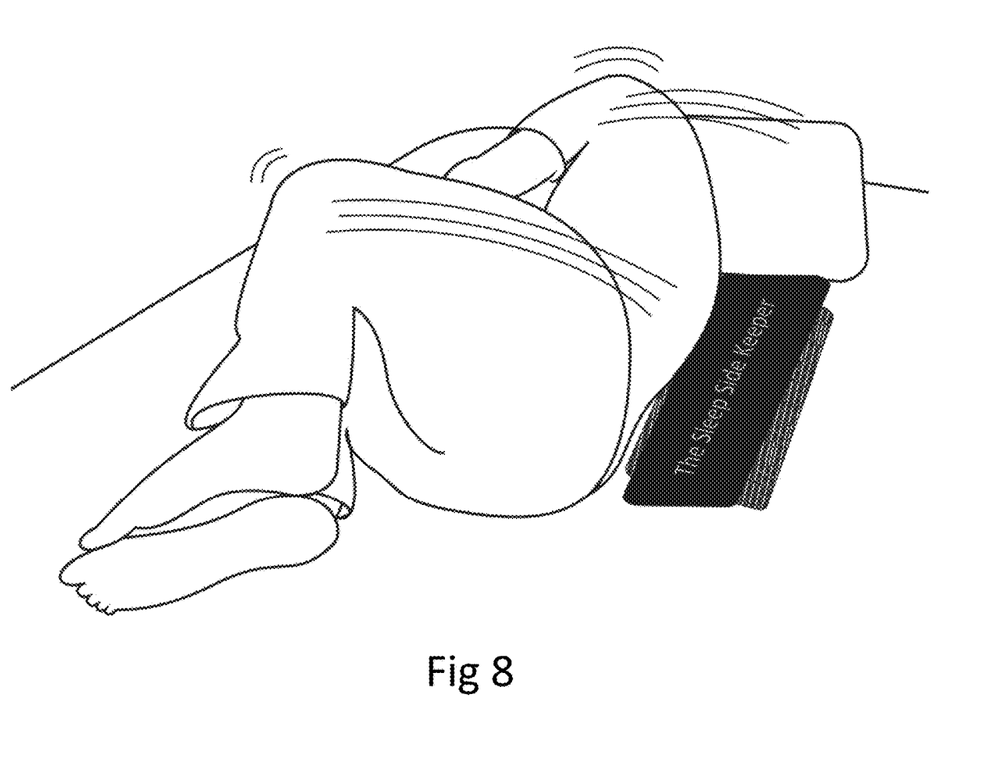
FIG. 8 shows the side sleeper returning to his original side sleeping position.
Figure 9:
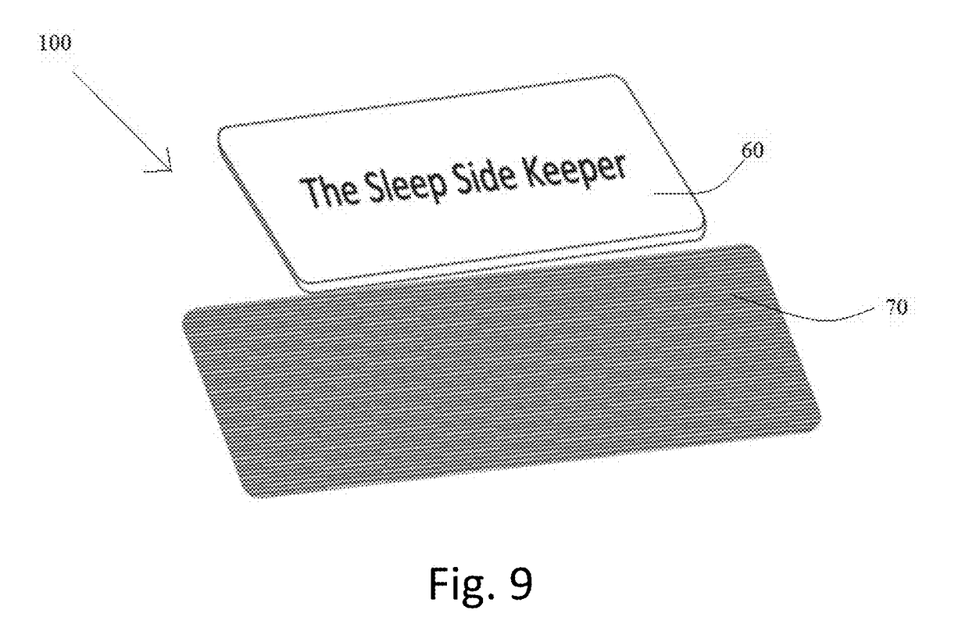
FIG. 9 shows the covered vibrating element and the non-slip rectangular strip of fabric of the present invention.

As seen in FIGS. 6-8, the present invention is used by first placing the non-slip rectangular strip of fabric 70 on a bed 200 at a position that will prevent a side sleeper from laying on it for a prolonged period, and lastly placing the pouch 60, after all of the elements of the anti-snoring system described above have been assembled and placed, in the pouch, on the non-slip rectangular strip of fabric 70.

The anti-snoring system 100 works by vibrating and creating a buzzing sound when a side sleeper turns and places his or her back on the anti-snoring system 100.

An advantage of the present invention is that it promotes side sleeping.

Another advantage of the present invention is that it prolongs the sleep cycle of a person who snores or suffers from sleep apnea.

Still another advantage of the present invention is that it allows a person who suffers from sleep apnea to reduce the chances of coming down with illnesses that are associated with sleep apnea.

Still another advantage of the present invention is that it allows a person who suffers from sleep apnea, to reduce the chances of coming down with any illness that is associated with sleep apnea.

While the inventor's above description contains many specificities, these should not be construed as limitations on the scope, but rather as an exemplification of several preferred embodiments thereof. Many other variations are possible. Accordingly, the scope should be determined not by the embodiments illustrated, but by the specification, the drawings, and the appended claims and their legal equivalents.

What is claimed is:

1. An anti-snoring system that aids individuals to sleep on their sides, the anti-snoring system comprises of:
    a rectangular plate;
    a raised rectangular frame that defines a rectangular aperture that is affixed to the rectangular plate;
    a rectangular printed circuit board that defines a plurality of sensors that are placed on a periphery of the rectangular printed circuit board, the rectangular printed circuit board has a first pair of vibrating motors and a second pair of vibrating motors, the vibrating motors are placed on the rectangular printed circuit board so that the first pair of the vibrating motors are linearly aligned on a first side of the rectangular printed circuit board and the second pair of the vibrating motors are linearly aligned on a second side of the rectangular printed circuit board, a battery receiver that is positioned at a central location of the rectangular printed circuit board, the rectangular printed circuit board operatively powers and connects the plurality of sensors, the first pair of vibrating motors, and the second pair of vibrating motors, a battery case that is affixed to the rectangular printed circuit board around the battery receiver, a first pair of raised adhesive rectangular strips attach to the first side of the rectangular printed circuit board and a second pair of raised adhesive rectangular strips attach to the second side of the rectangular printed circuit board, a first pair of flat covers attached to the first pair of raised adhesive rectangular strips, the first pair of flat covers cover at least two sensors and each of the first pair of flat covers define apertures that allow the first pair of vibrating motors to pass through them when the first pair of flat covers are pressed toward the rectangular printed circuit board, a second pair of flat covers attach to the second pair of raised adhesive rectangular strips, the second pair of flat covers cover at least two sensors and each of the second pair of flat covers define apertures that allow the second pair of vibrating motors to pass through them when the second pair of flat covers are pressed toward the rectangular printed circuit board, at least one battery is placed in the battery receiver, and a battery cover that removably covers the battery case;
    a pouch configured to cover the rectangular plate, the raised rectangular frame, the rectangular printed circuit board, the plurality of sensors, the first pair and second pair of vibrating motors, the battery receiver, the battery case, the first pair and the second pair of raised adhesive rectangular strips, the first pair and second pair of flat covers, the at least one battery, and the battery cover after they have all been assembled; and
    a non-slip rectangular strip of fabric configured to receive the pouch and be placed on a section of a bed or a sleeping surface, wherein when a user laying adjacent the section of the bed or sleeping surface rolls onto the system, the flat covers are configured to press onto the plurality of sensors thereby triggering the vibrating motors to vibrate and gently force the user to roll back into a position that they were in prior to rolling on the system.

2. The anti-snoring system that aids individuals to sleep on their sides of claim 1, wherein the battery cover attaches to the battery case via hook and loop fasteners.

3. The anti-snoring system that aids individuals to sleep on their sides of claim 2, wherein the plurality of sensors totals eight and two of the eight sensors are placed around each vibrating motor, and each flat cover covers two sensors, the flat covers do not touch the sensors unless a weight is applied to the flat covers.

4. The anti-snoring system that aids individuals to sleep on their sides of claim 1, wherein the pouch is comprised of an upper fabric cover that has hook and loop attachments around a periphery of the upper fabric cover and a lower fabric cover that has hook and loop attachments around a periphery of the lower fabric cover, the upper fabric cover and the lower fabric cover attach to each other.

5. The anti-snoring system that aids individuals to sleep on their sides of claim 1, wherein the rectangular plate is made of plastic.

* * * * *